(12) United States Patent
Sugano et al.

(10) Patent No.: US 9,377,461 B2
(45) Date of Patent: Jun. 28, 2016

(54) MONOCLONAL ANTIBODY AGAINST NECROSIS MARKER ERP29 AND USE THEREOF

(75) Inventors: Sumio Sugano, Minato-ku (JP); Yukari Kanzaki, Minato-ku (JP); Tsuneo Saga, Chiba (JP); Atsushi Tsuji, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 668 days.

(21) Appl. No.: 13/583,312

(22) PCT Filed: Mar. 8, 2011

(86) PCT No.: PCT/JP2011/055365
§ 371 (c)(1),
(2), (4) Date: Sep. 7, 2012

(87) PCT Pub. No.: WO2011/111698
PCT Pub. Date: Sep. 15, 2011

(65) Prior Publication Data
US 2013/0040311 A1 Feb. 14, 2013

(30) Foreign Application Priority Data
Mar. 8, 2010 (JP) ................................. 2010-050106

(51) Int. Cl.
| C07K 16/00 | (2006.01) |
| C12P 21/08 | (2006.01) |
| G01N 33/574 | (2006.01) |
| A61K 51/10 | (2006.01) |
| C07K 16/30 | (2006.01) |
| C07K 16/18 | (2006.01) |

(52) U.S. Cl.
CPC .......... *G01N 33/574* (2013.01); *A61K 51/1045* (2013.01); *C07K 16/18* (2013.01); *C07K 16/30* (2013.01); *G01N 2800/00* (2013.01)

(58) Field of Classification Search
None
See application file for complete search history.

(56) References Cited

U.S. PATENT DOCUMENTS

| 4,861,581 | A | 8/1989 | Epstein et al. |
| 5,019,368 | A | 5/1991 | Epstein et al. |
| 5,882,626 | A | 3/1999 | Epstein et al. |
| 6,017,514 | A | 1/2000 | Epstein et al. |
| 6,071,491 | A | 6/2000 | Epstein et al. |
| 6,827,925 | B1 | 12/2004 | Williams et al. |
| 2002/0052308 | A1* | 5/2002 | Rosen ................ C07K 14/4703 514/1 |
| 2003/0108963 | A1* | 6/2003 | Schlegel et al. ............... 435/7.23 |
| 2009/0191575 | A1 | 7/2009 | Watanabe et al. |
| 2010/0227317 | A1 | 9/2010 | Okatsu et al. |

FOREIGN PATENT DOCUMENTS

| EP | 0270340 | | 12/1987 |
| JP | 2733658 | B2 | 3/1998 |
| JP | 3190042 | B2 | 7/2001 |
| JP | 2002-519065 | A | 7/2002 |
| JP | 2008-14937 | A | 1/2008 |
| JP | 2009-519341 | | 5/2009 |
| JP | 2009524807 | | 7/2009 |
| WO | 93/09437 | A2 | 5/1993 |
| WO | 00/01822 | A1 | 1/2000 |
| WO | 2007/070538 | | 6/2007 |
| WO | 2007/085411 | A1 | 8/2007 |
| WO | 2008058192 | | 5/2008 |
| WO | 2009061832 | | 5/2009 |
| WO | 2010/004464 | | 1/2010 |
| WO | 2010143064 | | 12/2010 |
| WO | 2010146064 | | 12/2010 |
| WO | 2012100600 | | 8/2012 |

OTHER PUBLICATIONS

Non-Final Office Action for U.S. Appl. No. 13/583,524, dated Nov. 1, 2013.
Schulte et al., "Peroxiredoxin 4: a multifunctional biomarker worthy of further exploration", BMC Medicine, 9:137 (2011).
Lederman et al., "A single amino acid substitution in a common African allele of the CD4 molecule ablates binding of the monoclonal antibody, OKT4", Molecular Immunology, 28(11):1171-1181 (1991).
Coleman et al., "Effects of amino acid sequence changes on antibody-antigen interactions", Research Immunology, 145(1):33-36 (1994).
Abaza et al., "Effects of amino acid substitutions outside an antigenic site on protein binding to monoclonal antibodies of predetermined specificity obtained by peptide immunization: Demonstration with region 94-100 (Antigenic Site 3) of myoglobin", Journal of Protein Chemistry, 11(5):433-444 (1992).
Saito et al., "Turning point in apoptosis/necrosis induced by hydrogen peroxide", Free Radical Research, 40(6):619-630 (2006).
Schulte et al., "Immunoluminometric assay for quantification of peroxiredoxin 4 in human serum", Clinica Chimica Acta, 411(17-18):1258-1263 (2010).
Bambang et al., "Cytokeratin 19 regulates endoplasmic reticulum stress and inhibitors ERp29 expression via p38 MAPK/XBP-1 signaling in breast cancer cells", Experimental Cell Research, Academic Press, US, 315(11):1964-1974 (2009).
Bambang et al., "Overexpression of endoplasmic reticulum protein 29 regulates mesenchymal-epithelial transition and suppresses xenograft tumor growth of invasive breast cancer cells", Laboratory Investigation, 89(11):1229-1242 (2009).

(Continued)

*Primary Examiner* — Amy Juedes
(74) *Attorney, Agent, or Firm* — Sughrue Mion, PLLC

(57) ABSTRACT

[PROBLEM] To provide a monoclonal antibody against a biomarker which shows high specificity and can be effectively used in detection and diagnosis of various lesions relevant to various kinds of carcinomas and foci of necrosis, and so forth.
[MEANS] A monoclonal antibody against a necrosis marker consisting the following amino acid sequence: (1) the amino acid sequence of any of SEQ ID NOs: 1 to 3, or (2) an amino acid sequence having substitution, deletion and/or insertion of one or several amino acid residues in the amino acid sequence of (1) or sharing a homology of 90% or more with the amino acid sequence of (1), and showing the same function, activity or property as that of the amino acid sequence of (1) as a protein.

4 Claims, 5 Drawing Sheets

(56) References Cited

OTHER PUBLICATIONS

Gao et al., "ERp29 induces breast cancer cell growth arrest and survival through modulation of activation of p38 and upregulation of ER stress protein p58$^{IPK}$", Laboratory Investigation, 92(2):200-213 (2011).

Communication for EP 11753352 dated Jul. 31, 2013, with Supplementary European Search Report dated Jul. 25, 2013.

Communication for EP 11753356 dated Jul. 31, 2013, with Supplementary European Search Report dated Jul. 19, 2013.

Jian-Feng Lin et al., "Identification of candidate prostate cancer biomarkers in prostate needle biopsy specimens using proteomic analysis", Int. J. Cancer, 2007, pp. 2596-2605, vol. 121.

Guoan Chen et al., "Proteomic Analysis of Lung Adenocarcinoma: Identification of a Highly Expressed Set of Proteins in Tumors", Clinical Cancer Research, Jul. 2002, pp. 2298-2305, vol. 8.

Samuel Karlin et al., "Methods for assessing the statistical significance of molecular sequence features by using general scoring shemes", Proc. Natl. Acad. Sci. USA, 1990, pp. 2264-2268, vol. 87.

Samuel Karlin et al., "Applications and statistics for multiple high-scoring segments in molecular sequences", Proc. Natl. Acad. Sci. USA, 1993, pp. 5873-5877, vol. 90.

Stephen F. Altschul et al., "Gapped BLAST and PSI-BLAST: a new generation of protein database search programs", Nucleic Acids Research, 1997, pp. 3389-3402, vol. 25, No. 17.

Tatiana A. Tatusova et al., "BLAST 2 Sequences, a new tool for comparing protein and nucleotide sequences", FEMS Microbiology Letters, 1999, pp. 247-250, vol. 174.

William R. Pearson et al., "Improved tools for biological sequence comparison", Proc. Natl. Acad. Sci. USA, 1988, pp. 2444-2448, vol. 85.

Harish Chandra et al., "Proteome analysis of mouse macrophages treated with anthrax lethal toxin", Biochimica et Biophysica Acta, 2005, pp. 151-159, vol. 1747.

Stephen F. Altschul et al., "Basic Local Alignment Search Tool", J. Mol. Biol., 1990, pp. 403-410, vol. 215.

International Search Report for PCT/JP2011/055365 dated Apr. 19, 2011.

Office Action for Japanese Application No. 2011-049029 dated Jul. 8, 2014 (with English Language Excerpt).

Office Action for Japanese Application No. 2012-504472 dated Sep. 2, 2014.

Zhang et al., "ERp29 is a Radiation-Responsive Gene in IEC-6 Cell", Journal of Radiation Research, 49:587-596 (2008).

Bambang et al., "Cytokeratin 19 regulates endoplasmic reticulum stress and inhibitors ERp29 expression via p38 MAPK/XBP-1 signaling in breast cancer cells", Experimental Cell Research, Academic Press, US, 315(11):1964-1974 (2009a).

Bambang et al., "Overexpression of endoplasmic reticulum protein 29 regulates mesenchymal-epithelial transition and suppresses xenograft tumor growth of invasive breast cancer cells", Laboratory Investigation, 89(11):1229-1242 (2009b).

Gao et al., "ERp29 induces breast cancer cell growth arrest and survival through modulation of activation of p38 and upregulation of ER stress protein p58IPK", Laboratory Investigation, 92(2):200-213 (2011).

Schulte et al., "Immunoluminometric assay for quantification of peroxiredoxin 4 in human serum", Clinica Chimica ACTA 411:1258-1263 (2010).

Zhang et al., "Endoplasmic reticulum protein 29 (ERp29): An emerging role in cancer", International Journal of Biochemistry and Cell Biology, Pergamon, GB, 43(1):33-36 (2011).

Communication for EP 11753356.2 dated May 27, 2014.

Communication for EP 11753352.1 dated May 23, 2014.

International Search Report for PCT/JP2011/055356 dated Jun. 7, 2011.

Notification Concerning Transmittal of IPR on Patentability for PCT/JP2011/055356 dated Sep. 20, 2012, accompanied by the IPR on Patentability (dated Sep. 11, 2012) and the Written Opinion (dated May 24, 2011); with English Translation.

Notification Concerning Transmittal of IPR on Patentability for PCT/JP2011/055365 dated Sep. 20, 2012, accompanied by the IPR on Patentability (dated Sep. 11, 2012) and the Written Opinion (dated Apr. 6, 2011); with English Translation.

Wang et al., "TNF-related apoptosis-inducing ligand suppresses PRDX4 expression", FEBS Letters, 583:1511-1515 (2009).

Communication dated Mar. 30, 2015 from the European Patent Office in counterpart application No. 11753356.2.

Rainey-Barger et al., "Dimerization of ERp29, a PDI-like Protein, Is Essential for Its Diverse Functions," Molecular Biology of the Cell, Apr. 2007, vol. 18, pp. 1253-1260 (8 pages total).

Communication dated Apr. 28, 2015 from the Japanese Patent Office in counterpart application No. 2012-504472.

Office Action for Japanese Patent Application No. 2014-182176 dated Oct. 27, 2015.

Decision on Refusal for Japanese Application No. 2014-182176 dated May 17, 2016.

Cheretis et al., "Expression of ERp29, and Endoplasmic Reticulum Secretion Factor in Basal-Cell Carcinoma", Am J. Dermatopathol., 28(5):410-412 (2006).

Edwards et al., "Expressed sequence talgs and encoded human proteins", GenBank Accession No. CAE93822.1 (Sep. 6, 2000).

\* cited by examiner

A. Day 1 after Induction of Necrosis     B. Day 2 after Induction of Necrosis

C. Day 6 after Induction of Necrosis

Image of Cellulose-Membrane Electrophoresis

MONOCLONAL ANTIBODY AGAINST NECROSIS MARKER ERP29 AND USE THEREOF

CROSS REFERENCE TO RELATED APPLICATIONS

This application is a National Stage of International Application No. PCT/JP2011/055365 filed Mar. 8, 2011, claiming priority based on Japanese Patent Application No. 2010-050106 filed Mar. 8, 2010, the contents of all of which are incorporated herein by reference in their entirety.

TECHNICAL FIELD

The present invention relates to a novel necrosis marker, a method for detecting a focus of necrosis using amount of the necrosis marker, a kit for detecting a focus of necrosis containing a compound that specifically reacts with the necrosis marker, a composition for diagnostic imaging or conjugate for a therapeutic treatment comprising a compound that specifically reacts with the necrosis marker and a labeling compound or a compound effective for a therapeutic treatment, a kit for diagnostic imaging or pharmaceutical composition containing the conjugate, a method for identifying a necrosis marker, which comprises detecting necrosis relevant to a disease, and so forth.

BACKGROUND ART

Foci of necrosis are generally originate in cell death induced in a state that supply of nutrition and oxygen to cells of various tissues is reduced due to physical injury or obstruction, loss or reduction of blood supply. For example, in the case of solid carcinomas, when a carcinoma grows, supply of nutrition no longer spread over the whole carcinoma tissue, and as a result, a focus of necrosis is generated. Further, myocardial infarction and cerebral infarction are always accompanied by necrosis. Furthermore, postnecrotic cirrhosis, and necrotizing pancreatitis, in which oligotrophy and hypoxia are induced by mal blood flow, as well as necrotizing fasciitis, which is inflammation to be aggravated in subcutaneous tissues to the fascia, and so forth are also pathological conditions accompanied by foci of necrosis. In addition, arteriosclerotic gangrene, diabetic gangrene, and obstructive gangrene are also diseases relating to foci of necrosis.

Since foci of necrosis badly influence on surrounding tissues and cells, if it becomes possible to detect or diagnose condition or lesion of a necrosis part, or find such an aggravated lesion and perform a therapeutic treatment for that lesion as a target, it will be industrially useful.

However, prior art techniques concerning biomarkers for detecting a focus of necrosis are limited to the three kinds of antibodies selected by using insoluble intracellular antigens derived from a lymphoma cell line or lung cancer cell line (Patent document 1), an antibody against a soluble nuclear matrix protein (Patent document 2), an antibody or low molecular weight antibody specifically binding to the nucleus extract identified as a center of necrosis of a tumor and histone H1 (Patent document 3), and so forth. As markers for diagnosing severity including necrosis of a cardiovascular diseases-related tissue, inflammatory markers (CRP, TNF, IL-1, IL-6 etc.) are known. BNP is also used as a myocardial stress marker.

Further, as biomarkers of carcinomas, for example, peroxiredoxin 4 is known as a biomarker of pancreatic cancer and lung adenocarcinoma (Non-patent documents 1 and 2), and annexin A2 is known as a biomarker of large intestine carcinoma (Patent document 4). Furthermore, development of specific monoclonal antibodies against HMGB1, which is released from cell nuclei of necrotic cells, for use in therapeutic treatment is also advancing.

PRIOR ART REFERENCES

Patent Documents

Patent document 1: Japanese Patent No. 2733658
Patent document 2: Japanese Patent No. 3190042
Patent document 3: Japanese Patent Unexamined Publication (KOHYO) No. 2002-519065
Patent document 4: Japanese Patent Unexamined Publication (KOKAI) No. 2008-14937

Non-Patent Documents

Non-patent document 1: Lin J F, Xu J, Tian H Y, Gao X, Chen Q X, Gu Q, XuG J, Song J D, Zhao F K, Int. J. Cancer, 2007 Dec. 15; 121 (12):2596-605
Non-patent document 2: Chen G, Gharib T G, Huang C C, Thomas D G, Shedden K A, Taylor J M, Kardia S L, Misek D E, Giordano T J, Iannettoni M D, Orringer M B, Hanash S M, Beer D G, Clin. Cancer Res., 2002 July; 8(7):2298-305

SUMMARY OF THE INVENTION

Problem to be Solved by the Invention

However, any biomarker showing high specificity and effectively usable in detection and diagnosis of various lesions relating to various kinds of carcinomas and foci of necrosis has not been obtained yet.

The inventors of the present invention directed their attention to the fact that a focus of necrosis was generated in a state that nutrition and oxygen supply was reduced, then succeeded in identifying, as proteins characteristic to foci of necrosis or fragments thereof, proteins and fragments thereof that are expression products of 9 kinds of genes and having functions of such versatile necrosis markers as mentioned above from human cells cultured under undernutrition, hypoxia, high density and scaffold non-dependent conditions by using a disease proteomics technique based on fluorescence-labeled two-dimensional differential electrophoresis (2D-DIGE), mass spectrometry (MS) and N-terminal amino acid analysis, and thus accomplished the present invention.

Further, it was confirmed that antibodies against the aforementioned proteins could specifically recognize foci of necrosis in sections of lesion samples of breast cancer and lung cancer, and enabled distinguishable staining of them. Furthermore, it was demonstrated for the first time by the present invention that those antibodies labeled with an isotope could specifically recognize circumferences of a focus of necrosis in a cancer-bearing part of a nude mouse to which cancer cells were transplanted, and enabled imaging of them.

Means for Solving Problem

The present invention is thus embodied as follows.

Embodiment 1

A monoclonal antibody against a necrosis marker consisting of an expression product of a gene encoding: the amino acid sequence of any of SEQ ID NOs: 1 to 3, or an amino acid sequence having substitution, deletion and/or insertion of one or several amino acid residues in the amino acid sequence of any of SEQ ID NOs: 1 to 3 or sharing a homology of 90% or more with the amino acid sequence of any of SEQ ID NOs: 1 to 3, and showing the same function, activity or property as that of the amino acid sequence of any of SEQ ID NOs: 1 to 3 as a protein.

Embodiment 2

The monoclonal antibody according to Embodiment 1, wherein the necrosis marker consists of a partial polypeptide of a protein having the amino acid sequence of any of SEQ ID NOs: 1 to 3.

Embodiment 3

The monoclonal antibody according to Embodiment 1 or 2, which is produced by a hybridoma, NITE ABP-1063 (YK-ERp C6707 FCS(+)).

Embodiment 4

A method for detecting a focus of necrosis, which comprises measuring amount of a necrosis marker by using the monoclonal antibody according to any one of Embodiments 1 to 3.

Embodiment 5

The method according to claim 4, which comprises measuring a concentration of a necrosis marker contained in a sample which consists of one or more kinds of necrosis markers mentioned in any one of Embodiments 1 to 3, and detecting the focus of necrosis on the basis of increase of the measured concentration compared with a normal level as an indicator.

Embodiment 6

The method according to Embodiment 4 or 5, wherein whole blood or blood serum is used as the sample.

Embodiment 7

The method according to any one of Embodiments 4 to 6, wherein the focus of necrosis relates to a solid carcinoma, myocardial infarction, cerebral infarction, postnecrotic cirrhosis, necrotizing pancreatitis, necrotizing fasciitis, arteriosclerotic gangrene, diabetic gangrene, or obstructive gangrene.

Embodiment 8

A detection kit used for the method according to any one of Embodiments 4 to 7, which comprises the monoclonal antibody according to any one of Embodiments 1 to 3.

Embodiment 9

A conjugate for diagnostic imaging or a therapeutic treatment, which consists of a compound that specifically reacts with a necrosis marker consisting of an expression product of a gene encoding the amino acid sequence of any of SEQ ID NOs: 1 to 3, or an amino acid sequence having substitution, deletion and/or insertion of one or several amino acid residues in the amino acid sequence of any of SEQ ID NOs: 1 to 3 or sharing a homology of 90% or more with the amino acid sequence of any of SEQ ID NOs: 1 to 3, and showing the same function, activity or property as that of the amino acid sequence of any of SEQ ID NOs: 1 to 3 as a protein, and a labeling compound or a therapeutically effective compound.

Embodiment 10

A kit for use in diagnostic imaging or a pharmaceutical composition, which comprises the conjugate according to Embodiment 9 as an active component/ingredient.

Effect of the Invention

By measuring amount of the necrosis marker of the present invention in a sample, not only a focus of necrosis (tissue) in various solid carcinomas, myocardial infarction or cerebral infarction, but also a focus of necrosis in postnecrotic cirrhosis, necrotizing pancreatitis, necrotising fasciitis, etc. and further, a part to be a focus of necrosis in arteriosclerotic gangrene, diabetic gangrene, or obstructive gangrene can be detected.

Further, it was confirmed that foci of necrosis in sections of lesion samples of breast cancer and lung cancer could be distinguishably stained by using an antibody against a protein as the necrosis marker of the present invention or a fragment thereof, and thus it was concretely demonstrated that it is useful as a necrosis marker that can detect tissues of foci of necrosis in human breast cancer and lung cancer, positively.

Furthermore, it was demonstrated that the antibody labeled with an isotope could specifically recognize circumferences of a focus of necrosis in a cancer-bearing part of a nude mouse to which cancer cells were transplanted, and thereby enabled imaging of them.

BRIEF DESCRIPTION OF THE DRAWINGS

FIG. 1A shows the result obtained on the day 1 after the induction of necrosis, FIG. 1B shows the result obtained on the day 3 after the induction of necrosis, and FIG. 1C shows the result obtained on the day 6 after the induction of necrosis, which were all obtained through analysis by the 2D-DIGE method. The spots indicated with the arrows in FIG. 1C are the spots identified by the mass spectrometry and the N-terminal amino acid analysis, and the spot numbers correspond to the spot numbers (group) mentioned in Table 1.

DESCRIPTION OF EMBODIMENTS

Figure 1:
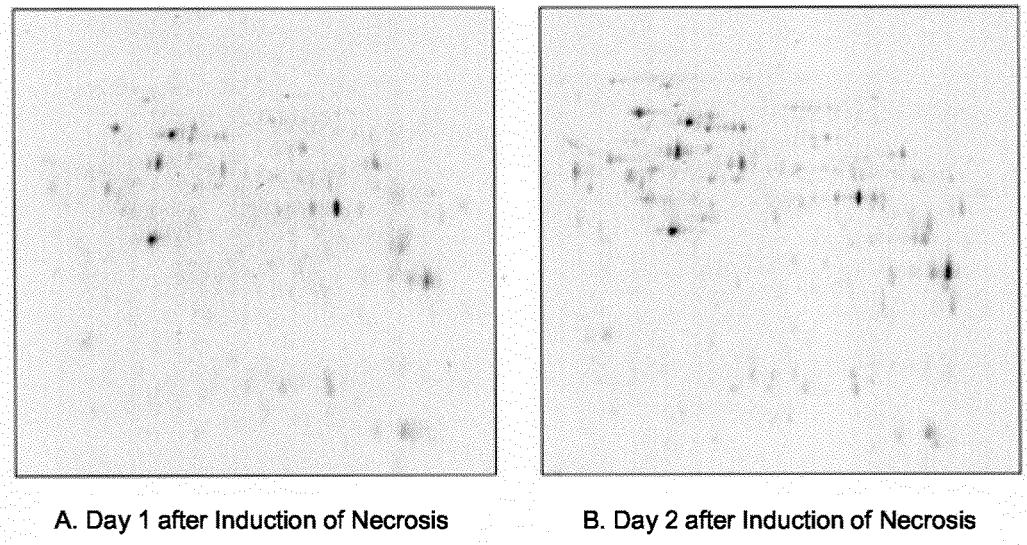
FIG. 1 shows photographs of gel on which proteomics analysis of purified cell extracts prepared from necrosis-induced HeLa cells and usually cultured HeLa cells was conducted by using the fluorescence-labeled two-dimensional differential gel electrophoresis (2D-DIGE) method in the examples of the present invention.
Figure 1:
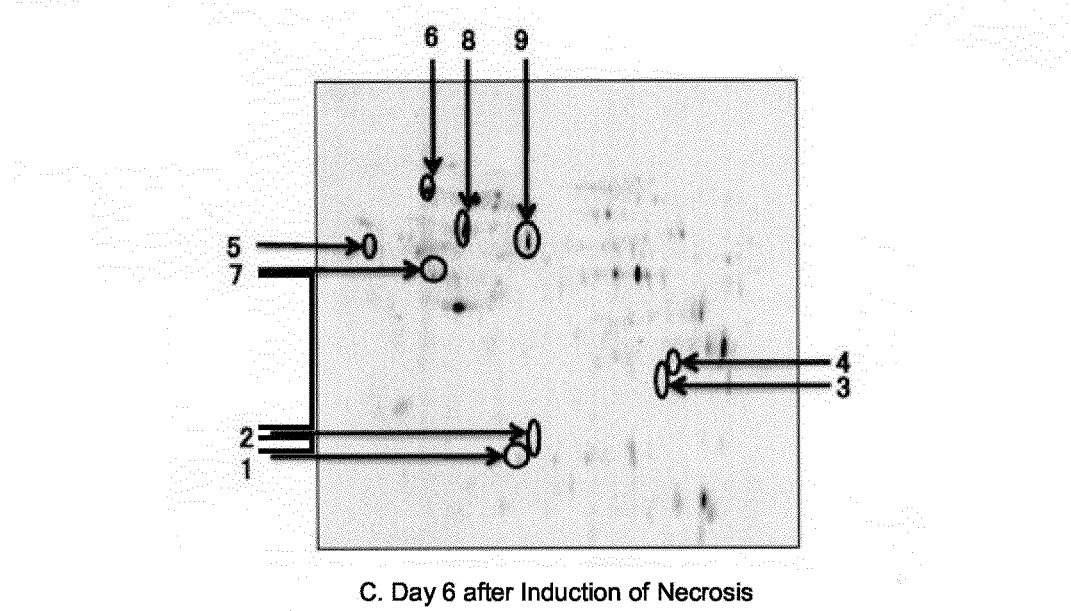

As described in the examples of this specification, the necrosis marker of the present invention can be obtained by identification and comparison of proteins expressed by human necrotic cells obtained by culturing appropriate human cells (for example, those of an established cultured cell line such as a HeLa cell strain, which is a cell strain of carcinoma of uterine cervix) under undernutrition, hypoxia, high density and scaffold non-dependent conditions and proteins expressed by the same cells cultured under usual culture conditions by using a disease proteomics technique based on fluorescence-labeled two-dimensional differential electrophoresis (2D-DIGE), mass spectrometry (MS) and N-terminal amino acid analysis, which are known to those skilled in the art.

Therefore, the present invention also provides a method for identifying a necrosis marker for detecting necrosis relevant to a disease. Thus, this method is characterized by comparing proteins expressed by necrotic cells obtained by inducing human cells by culturing under undernutrition, hypoxia, high density and scaffold non-dependent conditions and proteins expressed by the same cells cultured under usual culture conditions, and selecting a protein existing in the necrotic cells at a higher concentration (highly expressed) or a fragment thereof (limited degradation product or partial protein) as the necrosis marker.

In this specification, the "undernutrition, hypoxia, high density and scaffold non-dependent conditions" means, for example, a condition that the cells are cultured at a cell density of about $1 \times 10^7$ cells/ml for about 1 to 2 weeks without changing culture medium under an anaerobic condition in a tube with a lid in a state that the cells are suspended in a medium contained in the tube. On the other hand, the "usual culture conditions" mean that, for example, the cells are cultured at 37° C. and a cell density of $2 \times 10^4$ to $1 \times 10^5$ cells/ml in blood serum-containing DMEM medium (Dulbecco's modified Eagle medium) under a gas phase of 5% $CO_2$ and 95% air and saturated humidity. Further, the "protein existing at a higher concentration (highly expressed)" means, for example, a protein contained in a spot showing a twice or more higher fluorescence intensity in the fluorescence-labeled two-dimensional differential gel electrophoresis compared with that of the cells cultured under the usual culture condition, and increasing with time in the necrosis-induced cells.

As a result of such comparison as describe above, it was found for the first time that such 9 kinds (groups) of proteins as gene products as shown in Table 1 mentioned in the examples, peroxiredoxin 4, ERp29, VDAC-1, annexin A2, calreticulin, GRP78, PDIA6, HSP60 and ERp57, or partial polypeptides thereof existed in human necrotic cells at a significantly higher concentration compared with normal human cells cultured under the usual culture conditions. Although the genes thereof are known, it has not been known so far that they are specifically and highly expressed in a necrosis tissue.

Therefore, the aforementioned gene expression products or autoantibodies against the expression products are useful as necrosis markers.

Examples of such gene expression products usable as necrosis markers include, for example, proteins encoded by mRNA and cDNA of the genes, or a nucleic acid molecule containing a partial nucleotide sequence thereof, the proteins encoded by the genes and partial polypeptides thereof. For example, the proteins expressed from the aforementioned genes are useful as "necrotic focus-specific marker proteins" that are specifically and highly expressed in necrosis tissues.

More specifically, there can be mentioned the following amino acid sequences as amino acid sequences of the proteins encoded by the aforementioned genes:
(1) the amino acid sequence of any of SEQ ID NOs: 1 to 2,
(2) an amino acid sequence having substitution, deletion and/or insertion of one or several amino acid residues in the amino acid sequence of (1) or sharing a homology of 90% or more with the amino acid sequence of (1), and showing the same function, activity or property as that of the amino acid sequence of (1) as a protein Furthermore, as examples of the partial polypeptides of the proteins encoded by the genes, the partial polypeptides of ERp29 (any of SEQ ID NOs: 1 to 3) identified in Example 2 can be mentioned.

In order to determine homology (identity) of sequences in two amino acid sequences, the sequences are preliminarily optimized for the comparison. For example, a gap is inserted into one sequence to optimize the sequence for alignment with the other sequence. Then, amino acid residues or nucleotide residues at each position are compared. When an amino acid residue or nucleotide residue existing at a certain position in the first sequence is the same as that existing at the corresponding position in the second sequence, those sequences are identical for that position. Homology of two sequences is indicated in terms of percentage of the number of positions at which the sequences are identical to the total number of positions (total amino acid or nucleotide residues).

Homology of two amino acid sequences can be determined according to the aforementioned principle by using an arbitrary method known to those skilled in the art. For example, it can be determined by the algorithm of Karlin and Altshul (Proc. Natl. Acad. Sci. USA, 87:2264-2268, 1990 and Proc. Natl. Acad. Sci. USA, 90:5873-5877, 1993). The BLAST program utilizing the above algorithm was developed by Altshul et al. (J. Mol. Biol., 215:403-410, 1990). Further, Gapped BLAST is a program that can determine homology with higher sensitivity compared with BLAST (Nucleic Acids Res., 25:3389-3402, 1997). The aforementioned programs are mainly used in order to search databases for a sequence showing high homology to a given sequence. These are available, for example, on the web site on the Internet of U.S. National Center for Biotechnology Information.

Alternatively, as homology of sequences, a value determined by using the BLAST 2 Sequences software developed by Tatiana A., Tatusova et al. (FEMS Microbiol. Lett., 174:

247-250, 1999) can also be used. This software is available on the web site on the Internet of U.S. National Center for Biotechnology Information, or it can also be obtained. The programs and parameters to be used are as follows. In the case of an amino acid sequence, as parameters used in the Blastp program, Open gap: 11 and extension gap: 1 penalties, gap x_dropoff: 50, expect: 10, word size: 3, and Filter: ON are used. Furthermore, it is also possible to retrieve a sequence showing a homology from a database by using the more sensitive FASTA software (W. R. Pearson and D. J. Lipman, Proc. Natl. Acad. Sci. USA, 85:2444-2448, 1988). All of the values of the parameters are those used as default values on the web site.

The method for detecting a focus of necrosis according to the present invention comprises measuring amount of the aforementioned necrosis marker of the present invention. More specifically, the method comprises, for example, (1) measuring concentration of one necrosis marker selected from the necrosis markers of the present invention or an arbitrary combination thereof contained in a sample, and detecting a focus of necrosis on the basis of increase of the measured concentration compared with a normal level as an indicator.

The sample used for the method of the present invention is not particularly limited concerning origin, form, etc., so long as a sample derived from a living body possibly containing any of the aforementioned expression products from a focus of necrosis is used. Preferred examples include whole blood and blood serum.

Type, original tissue, etc. of a focus of necrosis detectable by the method of the present invention are not particularly limited, and examples include, for example, foci of necrosis relating to any one of various solid carcinomas, myocardial infarction, cerebral infarction, postnecrotic cirrhosis, necrotizing pancreatitis, necrotizing fasciitis, arteriosclerotic gangrene, diabetic gangrene, or obstructive gangrene.

The measurement of expression amount of the expression product of any one of the genes mentioned above may be quantitative, semi-quantitative, or qualitative depending on the method and principle of the measurement. Degree of the increase serving as an indicator should be significant difference in a parameter observable with types of the sample and the necrosis marker used in the detection method, the principle, conditions, etc. of the measurement means and method, and so forth. For example, in the case of quantitative measurement, it may be increase of 1.5 times or more compared with a normal level.

Amount of a protein or a partial polypeptide encoded by any of the aforementioned genes can be measured by an arbitrary method known to those skilled in the art. For example, it can be measured by immunological staining such as Western blotting using a suitable antibody, methods utilizing various kinds of immunological specific reactions such as EIA, amino acid sequence analysis methods for peptides such the method of using a gas phase sequencer based on the Edman method, and further, mass spectrometry, of which typical examples include MALDI-TOF/MS, ESI Q-TOF/MS, and so forth.

Among the aforementioned methods, the methods of measuring expression amount of a protein or a partial polypeptide thereof on the basis of an antigen-antibody reaction with an antibody specific to the protein or a partial polypeptide thereof, for example, Western blotting, and enzyme immunoassay such as EIA, are preferred.

Furthermore, there can be mentioned the method of measuring amount of the necrosis marker consisting of an autoantibody against the expression product on the basis of an antigen-antibody reaction using the protein as a gene expression product of any one of the aforementioned genes, or a partial polypeptide thereof as an antigen.

Therefore, the aforementioned antibody can be prepared by a suitable method known to those skilled in the art by using the protein, an appropriate partial polypeptide (peptide fragment) thereof, any of various derivatives or complexes thereof, or the like as an antigen substance or an immunogen. For example, such an antigen substance or an immunogen can be administered to an appropriate animal such as mouse, rat, rabbit, goat and fowl, and a polyclonal antibody can be prepared from antiserum of the animal. Alternatively, a monoclonal antibody can be prepared by a known method utilizing cell fusion according to known monoclonal antibody preparation methods (described in "Monoclonal Antibody", Nagamune H. and Terada H., Hirokawa Publishing Co., 1990; "Monoclonal Antibody", James W. Goding, Third edition, Academic Press, 1996, etc.).

Furthermore, there can also be mentioned various kinds of artificial antibodies having arbitrary forms known to those skilled in the art, for example, chimeric antibodies and humanized antibodies, which can be prepared by gene engineering techniques, as well as single chain antibodies, single chain variable region antibody fragment (scFv) consisting of the heavy chain variable domain having the heavy chain CDR 1-3 and light chain variable domain having light chain CDR 1-3 bonded with a linker, low molecular weight antibodies such as Fab fragment antibody and Fab' fragment antibody, and so forth. These can be easily produced by arbitrary methods known to those skilled in the art.

Such antibodies may be labeled with various labeling substances known to those skilled in the art, such as enzymes, radioisotopes, nanoparticles, fluorescent dyes and metal atoms.

Further, mRNA (or cDNA) of the aforementioned genes can be amplified or detected by the methods known to those skilled in the art, for example, various quantitative PCR methods such as RT-PCR using primers or probe appropriately designed on the basis of a nucleotide sequence of the genes, and real-time reverse transcription PCR (real-time RT-PCR), various kinds of microarray (DNA chip) techniques, and so forth. Detection and identification of a nucleic acid molecule amplified by the PCR method can be performed by an appropriate method such as a method of directly determining the nucleotide sequence (sequencing method), and a combination thereof with electrophoresis.

The nucleotide sequence of the aforementioned primers or probe preferably contains nucleotides in such a number that specific binding with a template is enabled, for example, 15 to 40 nucleotides, more specifically, it preferably contains about 15 to 25 nucleotides, and it is also important that the nucleotide sequence should be such a nucleotide sequence that any hairpin structure is not formed in the primers, or a sense strand and an antisense strand do not anneal to each other. It is also possible to use, for example, commercially available software for primer design such as Oligo™ (product of National Bioscience Inc.).

The detection kit used for the detection method of the present invention is characterized by comprising a compound that specifically reacts with the necrosis marker of the present invention. Preferred examples of such a compound include the aforementioned various antibodies.

The detection kit of the present invention can have a configuration suitable for the object of the measurement or the principle of the measurement. The kit may comprise, as the components thereof, for example, the aforementioned expression product, for example, an antibody specific to a protein or a partial polypeptide thereof, or a protein as an expression product that is an antigen for an autoantibody against the expression product or a partial polypeptide thereof, various kinds of second antibodies (labeled antibody), and a compound that specifically reacts with the expression product of the gene such as primers for amplification of the aforementioned mRNA (cDNA) and a probe for hybridization used in DNA chips (it consists of, for example, a nucleotide sequence comprising about 10 to 100 of continuous nucleotide residues). Furthermore, according to the configuration, use thereof, etc., the kit may contain other elements or components known to those skilled in the art, for example, various reagents, enzymes, buffers, reaction plates (vessel), and so forth. In addition, in order to make detection after the PCR reaction easy, it is preferred that a labeling substance such as arbitrary fluorescent substances known to those skilled in the art is bound to an end of at least one of these primers. Examples of suitable labeling substances include, for example, radiation labeling substances such as $^{32}$P, fluorescent substances such as cyanines including Cy3 and Cy5, 6-carboxyfluorescein (FAM), 4,7,2',4',5',7'-hexachloro-6-carboxyfluorescein (HEX), NED (Applied Systems Japan), and 6-carboxy-X-rhodamine (Rox), chemiluminescent substances, and so forth.

The materials, instruments, apparatuses, and so forth used for each of the aforementioned measurements are easily available by those skilled in the art, and procedure, conditions, etc. of each measurement operation can be suitably determined according to manuals attached to the instruments and apparatuses, or depending on the other conditions such as type of cells to be used.

Furthermore, a complex consisting of a compound that specifically reacts with the aforementioned necrosis marker such as the various kinds of antibodies against the necrosis marker already mentioned above and a labeling compound or a compound effective for a therapeutic treatment is useful, for example, for diagnostic imaging such as PET or SPECT, or as a drug for a therapeutic treatment (conjugate: complex). Examples of radionuclide effective for nuclear medicine diagnosis include, for example, positron emitting nuclides (Cu-64 etc.) and gamma-ray emitting nuclides (In-111 etc.). Further, examples of the labeling compounds include nuclides inducing electron anti-13 decay such as $^{15}$O, $^{13}$N, $^{11}$C, and $^{18}$F. Examples of the compound effective for a therapeutic treatment include arbitrary drugs known to those skilled in the art, for example, antitumor agents, and radionuclides that emit cytotoxic β-ray (Y-90 etc.).

Therefore, such a conjugate can be an active component/ingredient of a kit for diagnostic imaging or a pharmaceutical composition. Such a pharmaceutical composition can be formulated by the known pharmaceutical methods. For example, it is contemplated to formulate a pharmaceutical composition by combining the conjugate with a pharmacologically acceptable carrier or medium, specifically, by suitably combining with sterilized water, physiological saline, vegetable oil, emulsifier, suspending agent, surfactant, stabilizer, agent for sustained release, etc., and administer the composition. The pharmaceutical composition of the present invention may be in the form of aqueous solution, tablet, capsule, troche, buccal tablet, elixir, suspension, syrup, nasal drop, inhalation solution, or the like. Content of the compound of the present invention can be appropriately determined by those skilled in the art depending on the purpose of therapeutic treatment, route of administration, object of therapeutic treatment, and so forth.

EXAMPLES

Hereafter, the present invention will be explained in more detail with reference to examples. However, these examples do not limit the technical scope of the present invention at all. Those skilled in the art can implement various variations and modifications of the present invention without deviating from the technical scope of the present invention.

Isolation of Fatal Phenotype

There are various methods for identifying a cell having a fatal phenotype. In a necrotic cell or an apoptotic cell, change of cell morphology or cell permeability, i.e., "blebbing" of the cell membrane, is observed. Various dyes, stains, and antibodies can be used in such methods, and examples include propidium iodide and antibody Apo2.7, caspase dye, and so forth, but not limited to these.

Trypan Blue Staining

Trypan blue is a blue dye. Live cells having an intact membrane eliminate trypan blue from intercellular compartments, and therefore they are not stained. Since the cell membrane of dead cells or dying cells has permeability, cytoplasm is stained in blue.

Propidium Iodide Staining

Propidium iodide (PI) is a fluorescent DNA-intercalated molecule. Live cells having an intact membrane eliminate PI from intercellular compartments, and therefore they remain non-fluorescent. Dead cells or dying cells are infectible and permeable to PI, and they become fluorescent. PI staining is used for both necrotic cells and apoptotic cells.

Annexin V

Annexin V binds to a moiety of an anionic phospholipid such as phosphatidylserine. The cell membranes of live cells have the lipid bilayer structure, and phospholipids are unevenly distributed in the inner membrane and the outer membrane of the cell membrane. Phosphatidylserine usually localizes in the inner membrane. When many cells suffer from apoptosis, this lipid dislocates to the outer membrane of cells, and is exposed. By this dislocation, externally added fluorescence-conjugated annexin V is enabled to interact with the lipid, and thereby the cells suffering from apoptosis can be labeled. Then, by separating dead cells not labeled with the fluorescence-conjugated annexin V, necrotic cells can be separated.

Example 1

Preparation of Necrotic Focus Cell Model System

The method of the present invention requires a cell in which necrosis is induced as a cell model forming a focus of necrosis. Therefore, necrosis was induced in the cells of cervical cancer cell strain, HeLa cells, to prepare a cell model forming a focus of necrosis. The HeLa cells are generally adhesive cells, and $2 \times 10^5$ to $1 \times 10^6$ cells are cultured on a 10-cm$^2$ petri dish in a scaffold-dependent manner. In usual culture, they are cultured at 37° C. and a cell density of $2 \times 10^4$ to $1 \times 10^5$ cells/ml in 10 ml of blood serum-containing DMEM medium (Dulbecco's modified Eagle medium) under a gas phase of 5% $CO_2$ and 95% air and saturated humidity. The HeLa cells have high proliferation potency, and in the highly nutritious blood serum-containing DMEM medium, they proliferate to reach confluent in a 10-cm$^2$ petri dish within two to three days. Since the HeLa cells are cells of a cancer cell line, even if the cells reach confluent in a petri dish, they do not suffer from contact inhibition, and can proliferate. However, if they are excessively proliferated, they promptly undergo cell death. In the present invention, by culturing the HeLa cells at a high density of $1 \times 10^7$ cells/ml for about 1 to 2 weeks without changing culture medium under an anaerobic condition in a tube with a lid in a state that the cells are suspended in the medium contained in the tube without scaffold, undernutrition, hypoxia, high density and scaffold non-dependent conditions characteristic to the formation of a focus of necrosis were reproduced.

1.1 Induction of Necrosis in HeLa Cells

The HeLa cells were cultured in a usual manner in the DMEM medium (Gibco BRL) containing 100 units/ml of penicillin and streptomycin (Gibco BRL) and 10% FBS (JRH) contained in a 10-cm$^2$ petri dish. The proliferated HeLa cell were removed from the 10-cm$^2$ petri dish with trypsin-EDTA (Gibco BRL), and washed twice with ice-cooled PBS (−), and 1×10$^7$ cells were transferred to a 1.5-ml tube, and cultured for 15 days in 1 ml of the aforementioned DMEM medium or the DMEM medium not containing 10% FBS. A pH indicator was added to the medium to confirm decrease of oxygen concentration induced by oxygen consumption due to cellular respiration from the day 3, but the culture was continued with the lid.

1.2 Isolation of Fatal Phenotype 1.2.1 Trypan Blue Staining

The necrosis-induced HeLa cells were collected by centrifugation, and washed twice with ice-cooled PBS(−). The collected HeLa cells were suspended in ice-cooled PBS(−) at a density of about 1×10$^6$ cells/ml, a 0.4% trypan blue/PBS buffer solution (Gibco BRL) in a $\frac{1}{10}$ volume was added to the suspension and mixed, and the mixture was incubated at room temperature for 3 to 5 minutes, and then observed under a microscope. Colorless live cells as well as dead cells and dying cells stained in blue were counted.

Among the HeLa cells in which necrosis was induced by the aforementioned method, 13.9% of the cells in the serum-free DMEM medium and 20.6% of the cells in the blood serum-containing DMEM medium after the day 1 of the culture, 79.5% of the cells in the serum-free DMEM medium and 68.5% of the cells in the blood serum-containing DMEM medium after the day 2 of the culture, and 91.5% of the cells in the serum-free DMEM medium and 81.2% of the cells in the blood serum-containing DMEM medium after the day 3 of the culture were stained in blue, and thus confirmed to be dead cells. Thereafter, the cells were cultured for 15 days, and it was confirmed that about 90% of the cell population consisted of dead cells.

1.2.2 Staining of Dead Cells with Fluorescent Dye Label

As cells having a fatal phenotype, roughly speaking, those undergone necrosis and those undergone apoptosis (programmed cell death) can be supposed. It is considered that, in a focus of necrosis, the ratio of necrotic cells is larger than that of apoptotic cells, and in order to distinguish the cell death, the cells were further stained with a fluorescent dye. The necrosis-induced HeLa cells were collected by centrifugation, and washed twice with ice-cooled PBS(−). To the collected cells, 100 µl of a staining Hepes buffer solution (10 mM Hepes-NaOH (pH 7.4), 140 mM NaCl, 5 mM CaCl$_2$) containing annexin V (Annexin-V-Fluos, final concentration: 20 µl/ml, Roche) and propidium iodide (PI, final concentration: 1 µg/ml, Dojin Chemical Laboratory, Inc.) was added, and the mixture was incubated at room temperature for 10 to 15 minutes, and observed under a fluorescence microscope (excitation: 488 nm, detection: 515 to 565 nm). The HeLa cells cultured on the 10-cm$^2$ petri dish were then cultured for 1 hour in the 10% FCS-containing DMEM medium containing 1 mM hydrogen peroxide, washed twice with ice-cooled PBS (−), then returned to the usual 10% FCS-containing DMEM medium, and cultured for 5 hours to induce apoptosis. These HeLa cells were similarly stained with Annexin-V-Fluos and PI, and observed under a fluorescence microscope.

In the HeLa cells cultured for 6 days in the 10% FCS-containing DMEM medium to induce necrosis, the nuclei were stained with PI. On the other hand, in the HeLa cells in which apoptosis was induced, regions around the cell membranes were strongly stained with annexin V, and a part of the cells were also stained with PI. The live cells prepared by usual culture were stained with neither PI nor annexin V. On the basis of these results, it was confirmed that the dead cells produced by the aforementioned method were necrotic cells.

Example 2

Identification of Marker Molecules Specific to Focus of Necrosis 2.1 Preparation of Cell Extracts The HeLa cells on the day 1 to day 6 after the induction of necrosis in the DMEM medium containing 10% FCS and the HeLa cells cultured in the usual manner obtained in Example 1 were collected, and washed twice with ice-cooling PBS(−). An ice-cooled solubilization buffer (20 mM Tris-HCl (pH 7.5), 150 mM NaCl, 1 mM EDTA, 1% NP-40) in a volume of 500 to 1,000 µl was added to the cells to suspend the cells, and the suspension was transferred to a 1.5-ml tube. The soluble fraction of the cells was extracted with rotating the tube at 4° C. for 30 minutes, and centrifuged at 15,000 rpm for 15 minutes, and the supernatant was collected as a cell extract. The collected cell extract was purified by using 2D-Clean up kit (80-6484-51, Amersham) according to the attached protocol, and dissolved in an appropriate volume of a lysis buffer (30 mM Tris (pH 8.5) 7 M urea, 2 M thiourea, 4% CHAPS, 5 mM magnesium acetate), the solution was centrifuged, and the supernatant was collected as a purified cell extract.

2.2 Quantification of Proteins

The proteins contained in the purified cell extract were quantified by the Bradford method using Protein Assay Reagent (500-0006, Bio-Rad) according to the attached protocol. Specifically, 1 µl of 0.1 N HCl and 8 µl of purified water were added to 1 µl of the purified cell extract to prepare a sample solution. As protein standard solutions, BSA Solution (23209, Thermo) was diluted to concentrations of 0.25 to 1 mg/ml, 1 µl of the lysis buffer and 1 µl of 0.1 N HCl were added to 1 µl of each standard solution to obtain a total volume of 10 µl. In a similar manner, 1 µl of the lysis buffer and 1 µl of 0.1 N HCl were added to 8 µl of purified water to prepare a blank solution. To each of the sample solution, the standard solutions and the blank solution, 200 µl of the Protein Assay reagent diluted 5 times was added, and sufficiently mixed, and the mixture was left at room temperature for 5 minutes. Absorbance of the mixture was measured at a wavelength of 595 nm within 1 hour after mixing the Protein Assay reagent, a calibration curve was prepared from the absorbance values of the BSA standard solutions, and amount of proteins contained in the purified cell extract was calculated.

2.3 Proteomics Analysis Using Fluorescence-Labeled Two-Dimensional Differential Gel Electrophoresis (2D-DIGE) Method The purified cell extracts prepared from the HeLa cells cultured in a usual manner and those on the days 1 to 6 after induction of necrosis in an amount of 25 µg each were separately labeled with Cy3 (CyDye DIGE Fluor Cy3, GE Healthcare) and Cy5 (CyDye DIGE Fluor Cy5, GE Healthcare), and 10 mM lysine (SIGMA) was added to terminate the fluorescence-labeling reaction. Equal volumes of HeLa cell purified extracts labeled with Cy3 and Cy5 were mixed, a sample buffer for one-dimensional electrophoresis (8 M urea, 2% CHAPS, 0.5% IPG buffer (17-6004-40, GE), 0.002% bromothymol blue solution) was added and sufficiently mixed, the mixture was centrifuged at 15,000 rpm for 5 minutes, and the supernatant was collected as a sample solution. A gel of 24 cm for the first dimensional electrophoresis (Immobiline DryStrip pH 3-11NL, 17-6003-77, GE Healthcare) having an ion gradient of pH 3 to 11) was swelled in the sample solution for 12 hours. The proteins contained in the purified cell extract were separated by isoelectric focusing by using an isoelectric focusing system for first dimensional electrophoresis (Ettan IPGphor 3 IEF System, GE Healthcare) with gradually elevating the voltage. Then, the intracellular solubilized proteins were further separated according to the molecular weight by the second dimensional electrophoresis using a 10% polyacrylamide gel (Acrylamide: 17-1310-01, GE Healthcare). The fluorescence-labeled proteins separated by the two-dimensional electrophoresis were detected with a variable image analyzer (Typhoon TRIO+, GE Healthcare). The spots on the gel images were analyzed by using analysis software for 2D-DIGE, DeCyder (GE Healthcare), and protein expressions in the cells were compared.

As a result of analysis of about 3,000 spots of proteins expressed in the HeLa cells in which necrosis was induced, 0.6% of proteins of which expression increased compared with that observed in the cells cultured in a usual manner and 0.4% of proteins of which expression decreased compared with the same were observed on the day 1 after the induction of necrosis (FIG. 1A), and 1.1% of proteins of which expression increased and 3.4% of proteins of which expression decreased compared with the same were observed on the day 3 after the induction of necrosis (FIG. 1B). Furthermore, as for expression of proteins of the intracellular soluble fraction, expression of 5.1% of the proteins increased, and expression of 2.9% of the proteins decreased compared with that observed in the cells cultured in the usual manner on the day 6 after the induction of necrosis (FIG. 1C).

2.4 Identification of Proteins by Mass Spectrometry

The proteins of which expression amounts increased in the HeLa cells in which necrosis was induced were identified by MALD-TOF/MS. Specifically, the 10% polyacrylamide gel after the aforementioned two-dimensional electrophoresis was electrified with a constant current of 2 mA/cm$^2$ of gel area for 90 minutes in a buffer of Tris, 6-aminocaproic acid and methanol system to electrically blot the proteins in the gel on a PVDF membrane (ProBlott (registered trademark), ABI). The proteins on the PVDF membrane were visualized by staining with Coomassie blue R-350 (17-0518-01, GE Healthcare), and the objective spots were excised with a razor, and digested with 1 fmol of lysyl endopeptidase (125-05061, Wako) at 37° C. for 16 hours. The obtained fragmented peptides were purified with a NuTip pipette tip (registered trademark, Glygen Corp.), and analyzed by MALD-TOF/MS (Voyager-DE™ PRO, AB SCIEX). The obtained fragments were compared with those in a database for protein analysis to obtain information concerning the obtained proteins.

2.5 Analysis of N-Terminal Amino Acids

N-Terminal amino acids of the proteins of which expression amount increased in the necrosis-induced HeLa cells were decomposed one by one by the Edman degradation to determine the primary structures. Specifically, the PVDF membranes on which the proteins obtained in the section 2.4 mentioned above were blotted was stained with Coomassie blue R-350 (GE), and the objective spots were excised with a razor, and each transferred to a 1.5-ml tube. After the PVDF membrane was wetted with a small volume of acetonitrile, a washing operation of adding 1 ml of Milli-Q water, vigorously stirring the mixture, and then removing Milli-Q water was repeated 5 times, and the amino acid sequence was automatically analyzed with a full automatic protein primary structure analyzer (PPSQ33A, Shimadzu).

As a result, among the proteins identified as markers specific to focus of necrosis, the primary sequences of N-terminal amino acids (9 amino acids) of the peroxiredoxin 4 fragment and the ERp29 fragment were identified as follows.

(1) Peroxiredoxin 4: WETEERPRT (SEQ ID NO: 4)
(2) ERp29: LHTKGALPL (SEQ ID NO: 5).

On the basis of the results mentioned above, among the spots showing a fluorescence intensity twice or more higher than that of the HeLa cells cultured in a usual manner and increasing over time in the necrosis-induced HeLa cells, 9 kinds (groups) of marker proteins specific to focus of necrosis (including limitedly degraded and partial proteins) were identified as the necrosis markers of the present invention as shown in Table 1 mentioned below. Some of the proteins shown in Tables 1 and 2 have a plurality of GI (GenBank Identifier) numbers. This is because the proteins, precursors and mutants thereof show the same results in mass spectrometry.

TABLE 1

| | Protein (gene) | SEQ ID NO | Name of identified sequence (Genbank identifier number) |
|---|---|---|---|
| 1 | Peroxiredoxin 4 | | 1-A) Peroxiredoxin 4: PRDX4 (gi 49456297) |
| 2 | ERp29 | | 2-A) Endoplasmic reticulum protein 29 isoform 1 precursor (gi 5803013) |
| | | | 2-B) Chain A, Crystal structure of the protein-disulfide isomerase related chaperone 29 (gi 192987144) |
| | | 3 | 2-C) Endoplasmic reticulum protein 29. isoform CRA_b (gi 119618398) |
| 3 | VDAC-1 | | 3-A) Voltage-dependent anion-selective channel protein 1 (gi 4507879) |
| | | | 3-B) Porin 31HM (gi 238427) |
| | | | 3-C) Porin isoform 1 (gi 6063691) |
| | | | 3-D) Chain A, Solution structure of human Vdac-1 in Ldao Micelles (gi 198443050) |
| | | | 3-E) Chain A, Structure of the human Voltage-Dependent Anion Channel (gi 209447280) |
| 4 | Annexin A2 | | 4-A) Annexin A2 (gi 73909156) |
| | | | 4-B) Chain A, Structure of Human Annexin A2 in the presence of calcium ions (gi 56967118) |
| | | | 4-C) Annexin A2 isoform 2 (gi 4757756) |
| | | | 4-D) Chain A. Annexin A2 (gi 56966699) |
| | | | 4-E) Full-Putative annexin A2-like protein (gi 205830271) |
| | | | 4-F) Annexin A2 isoform 1 (gi 50845388) |

TABLE 1-continued

| Protein (gene) | SEQ ID NO | Name of identified sequence (Genbank identifier number) |
|---|---|---|
| 5 Calreticulin | | 5-A) Calreticulin precursor (gi 4757900) |
| | | 5-B) Calreticulin precursor variant (gi 62897681) |
| | | 5-C) Calreticulin, isoform CRA_a (gi 119604736) |
| 6 GRP78 | | 6-A) GRP78 precursor (gi 386758) |
| | | 6-B) Heat shock 70 kDa protein 5 (gi 16507237) |
| | | 6-C) Bip protein (gi 6470150) |
| | | 6-D) 78 kDa glucose-regulated protein (gi 2506545) |

TABLE 2

| Protein (gene) | SEQ ID NO | Name of identified sequence (Genbank identifier number) |
|---|---|---|
| 7 PDIA6 | | 7-A) protein disulfide isomerase-related protein 5 (gi 1710248) |
| | | 7-B) protein disulfide isomerase A6 precursor (gi 5031973) |
| | | 7-C) unnamed protein product (gi 193785970) |
| | | 7-D) unnamed protein product (gi 34534342) |
| 8 Heat shock 60 kDa protein 1 | | 8-A) Heat shock protein 60 (gi 77702086) |
| | | 8-B) Chaperonin (gi 31542947) |
| | | 8-C) Mitochondrial heat shock 60 kD protein 1 variant 1 (gi 189502784) |
| 9 ERp57 | | 9-A) ER-60 protease (gi 1208427) |
| | | 9-B) Protein disulfide isomerase (gi 860986) |
| | | 9-C) Protein disulfide-isomerase A3 precursor (gi 21361657) |
| | | 9-D) ER-60 protein (gi 2245365) |
| | | 9-E) Protein disulfide isomerase family A, member 3, isoform CEA_a (gi 119597640) |
| | | 9-F) Phospholipase C-alpha (gi 303618) |

2.6 Identification of Proteins by Western Blotting

Among the necrotic focus-specific marker proteins shown in Table 1, which were identified by mass spectrometry and N-terminal amino acid analysis, five kinds of them mentioned below, for which commercial antibodies were available, were confirmed by Western blotting. Specifically, non-specific adsorption on the PVDF membrane obtained in the section 2.4 on which the proteins mentioned above were blotted was blocked by using Block Ace (UK-B80, DS Pharma Biomedical), then primary antibodies diluted with PBS(−) to an optimum concentration (100 to 2,000 times) were added, and the reaction was allowed at room temperature for 1 hour with gentle shaking. After three times of washing with PBST, a biotin-labeled anti-IgG antibody (BA-1400, VECTASTAIN) was added, and the reaction was allowed at room temperature for 30 minutes with gentle shaking. After three times of washing with PBST, an avidin/biotin-labeled horseradish peroxidase complex solution (VEC) was added, and the reaction was allowed at room temperature for 30 minutes with gentle shaking. After three times of washing with PBST, a solution of 3,3'-diaminobenzidine (DAB, SK-4105, VEC), which is a substrate of the peroxidase, was added, and when a color development signal was observed, the PVDF membrane was transferred into Milli-Q water to terminate the color development. As negative controls, Western blotting was performed in the same manner by using a blocking peptide of anti-Bip antibody (#1084, Cell Signaling) for the anti-Bip antibody, anti-rabbit IgG control antibody for the anti-peroxiredoxin 4, anti-calreticulin, and anti-ERp57 antibodies, and anti-rabbit IgG control antibody for the anti-ERp29 antibody.

Primary Antibodies Used (1) Peroxiredoxin 4: peroxiredoxin 4 antibody [7A1], ab 16943, Abcam (spot number 1)

(2) ERp29: ERp29 antibody, ab40982, Abcam (spot number 2)

(3) Calreticulin: calreticulin mouse mAb, ab54922, Abcam (spot number 5)

(4) Bip: Bip (C50B12) Rabbit mAb, #3177, Cell Signaling (spot number 6)

(5) ERp57: Monoclonal anti-ERp57 (TO-2), E5031, SIGMA (spot number 9)

By Western blotting, the five spots among the nine spots identified by MS and N-terminal amino acid analysis were confirmed to be those of peroxiredoxin 4, ERp29, calreticulin, Bip, and ERp57.

Example 3

Preparation of Monoclonal Antibodies 3.1 Sensitization of Immunized Animal and Cell Fusion For the peroxiredoxin 4 fragment and the ERp29 fragment among the proteins identified as necrotic focus-specific markers, mouse monoclonal antibodies that could recognize each sequence were prepared on the basis of the N-terminal amino acid sequences identified in Example 2.

A peptide of 10 residues consisting of the aforementioned N-terminus 9 amino acid residues of the peroxiredoxin 4 fragment or the ERp29 fragment and a cysteine residue added to the C-terminus of the foregoing residues for binding with a carrier polymer (KLH) was chemically synthesized in a conventional manner in an amount of about 10 mg, and purified by HPLC, and the purified peptide was used as an antigen peptide. The antigen peptide was crosslinked with KLH in a conventional manner, and mixed with an equal amount of the Freund's complete adjuvant (RM606-1, Mitsubishi Chemical Iatron), and the mixture was emulsified and used as an immunogen. The immunogen was administered to female mice of groups each consisting of two mice in an amount of 50 μg per mouse. As the immunization, short-term immunization consisting of 3 times of subcutaneous administration of the immunogen into foot pads of mice every two days and following sensitization for ten days, and long-term immunization consisting of 3 times of subcutaneous administration of the immunogen into the same every one week and following sensitization for 3 weeks were performed. In the case of the short-term immunization, a few hypertrophied lymph nodes were extracted on the day 10 after the start of the immunization, and the lymphocytes contained in them were fused with the myeloma cells P3U1. In the case of the long-term immunization, mouse lymph nodes were extracted on the day 21 after the start of the immunization in a manner similar to that used for the short-term immunization, and the lymphocytes contained in them were fused with the myeloma cells P3U1.

As a result of the cell fusion of the lymphocytes prepared from each two mice subjected to the short-term immunization and the long-term immunization with the immunogen consisting of the antigen peptide of the peroxiredoxin 4 fragment or the ERp29 fragment crosslinked with KLH and the myeloma cells of the cell strain P3U1, colonies were formed in about 800 wells for each case.

3.2 Screening of Hybridomas by ELISA

The hybridomas obtained by the cell fusion were cultured on a 96-well plate, and selected by using a usual HAT medium. The screening was performed by determining whether the culture supernatant of the well in which colony formation was observed contained antibodies that bound with the antigen peptide of the immunogen by ELISA. A peptide consisting of the N-terminal peptide of the peroxiredoxin 4 fragment+cysteine (WETEERPRTC (SEQ ID NO: 6)) or the N-terminal peptide of the ERp29 fragment+cysteine (LHTKGALPLC (SEQ ID NO: 7)), or an N-terminal 8-residue peptide of the peroxiredoxin 4 fragment (WETEERPR (SEQ ID NO: 8)) or an N-terminal 8-residue peptide of the ERp29 fragment (LHTKGALP (SEQ ID NO: 9)), which were newly chemically synthesized and purified by HPLC, was diluted with PBS(−) to a concentration of 200 μg/ml, and the solution was added to wells of a 96-well immunoplate (Maxisorp, Nunc) in a volume of 50 μl per well. The plate was left standing at 4° C. overnight to fix the synthetic peptide to the plate, washed twice with PBS(−), blocked at room temperature for 1 hour with Block Ace (DS Pharma Biomedical), and washed twice with PBS(−) containing 0.1% Triton-X 100 (PBST). The culture supernatant (100 μl) of each well in which colony formation was observed was added, and the plate was incubated at room temperature for 1 hour, and then washed twice with PBST. After the reaction with biotin-labeled anti-mouse IgG antibody (BA-1400, VEC) was allowed at room temperature for 30 minutes, the plate was washed 3 times with PBST. Further, the reaction with an avidin/biotin-labeled peroxidase complex solution (Mouse IgG ABC Kit, VECTASTAIN) was allowed at room temperature for 30 minutes, the plate was washed 3 times with PBST, then a solution of 2,2'-azino-bis(3-ethylbenzothiazoline-6-sulfonic acid) (ABTS, SK-4500, VEC), which is a substrate of the peroxidase, was added, and incubation was performed at room temperature until color development was observed. Then, an absorption signal generated by each clone was evaluated by measuring the absorbance at a wavelength of 405 nm using a microplate reader. Wells showing a high titer were selected, and monoclonal antibody-producing hybridomas were cloned by the limiting dilution method.

As a result of the primary screening of the hybridoma culture supernatants obtained from the peroxiredoxin 4 fragment-immunized mice, antibodies that recognized the antigen peptide consisting of the N-terminal peptide of the peroxiredoxin 4 fragment (9 amino acid residues) to which cysteine was added, and did not recognize KLH were produced in 2 wells in the case of the short-term immunization, and 33 wells in the case of the long-term immunization. Since the identified N-terminus of the peroxiredoxin 4 fragment differed from the site to be cleaved by usual limited degradation, antibodies that recognized this N-terminus sequence were considered to be necrotic focus specific. In order to further limit the recognition site, two kinds of peptides for negative screening of which N-terminus was masked ((Ac)WETEERPRTC (SEQ ID NO: 6), GAVQGWETEERPRTC (SEQ ID NO: 10)) were chemically synthesized in a conventional manner, purified by HPLC, crosslinked with KLH, fixed on a 96-well plate and used to perform secondary screening by ELISA. As a result, antibodies that recognized the identified N-terminus (WETEERPRTC (SEQ ID NO: 6)), but did not recognize the two kinds of peptides for negative screening crosslinked with KLH ((Ac)WETEERPRTC (SEQ ID NO: 6)-KLH and GAVQGWETEERPRTC (SEQ ID NO: 10)-KLH) and KLH were produced in 1 well in the case of the short-term immunization, and 31 wells in the case of the long-term immunization, among the wells selected by the primary screening. Among these wells, antibodies that further recognized N-terminal 8 amino acid residues were produced in 3 wells in the case of the long-term immunization, but no well in the case of the short-term immunization. Therefore, from the wells of the hybridomas obtained from the mice subjected to the long-term immunization, 5 wells showing a high titer including the three wells in which antibodies that recognized the N-terminal 8 amino acid residues were selected, and cloning was performed by the limiting dilution method to obtain 5 clones of anti-peroxiredoxin 4-specific monoclonal antibody-producing hybridomas.

Further, as a result of the primary screening of the hybridoma supernatants obtained from the mice immunized with the ERp29 fragment, antibodies that recognized the antigen peptide consisting of the N-terminal peptide of the ERp29 fragment (9 amino acid residues) to which cysteine was added, and did not recognize KLH were produced in 39 wells in the case of the short-term immunization, and 21 wells in the case of the long-term immunization. Among these wells, antibodies that further recognized the N-terminal 8 amino acid residues were produced in 7 wells in the case of the short-term immunization, and 5 wells in the case of the long-term immunization. Among them, two wells showing a high titer and derived from the short-term immunization, and three wells showing a high titer and derived from the long-term immunization were selected, and cloning was performed by the limiting dilution method to obtain 5 clones of anti-ERp29 fragment-specific monoclonal antibody-producing hybridomas.

Example 4

Staining of Necrotic Focus and Circumferential Tissues Thereof Using Monoclonal Antibodies and Commercially Available Antibodies 4.1 Histo-Immunological Staining The antibodies that recognized the necrotic focus-specific marker proteins were evaluated by using tissue sections of cancerous regions and non-cancerous regions of human breast cancer tissues (N=5), and cancerous regions and non-cancerous regions of human lung cancer tissues (N=5). Paraffin-embedding sections of tissue samples derived from breast cancer patients and lung cancer patients were obtained from Medical & Biological Laboratories. The paraffin embedding sections of the tissues were deparaffinized in a conventional manner by using xylene and ethanol, and the tissue sections were washed 3 times with PBS(−). The antigen was activated with a 10 mM citrate buffer (pH 6.0), endogenous peroxidase was inactivated by leaving the sections standing in 0.3% $H_2O_2$ for 30 minutes, and non-specific adsorption was blocked with horse serum. The antibodies against a necrotic focus marker (monoclonal antibody that recognized the N-terminal peptide of the peroxiredoxin 4 fragment or the N-terminal peptide of ERp29 fragment (one clone among each 5 clones finally obtained in Example 3), and the five kinds of commercial antibodies mentioned in Example 2) were each diluted with PBS(−) to an optimum concentration (250 to 1,000 times), and reacted with the blocked tissue section at room temperature for 1 hour, the section was washed 3 times with PBS(−), and the reaction with a biotin-labeled anti-IgG antibody (BA-1400, VEC) was allowed at room temperature for 30 minutes. After the tissue section was washed 3 times with PBS(−), the reaction with an avidin/biotin-labeled horseradish peroxidase complex (VEC) was allowed at room temperature for 30 minutes. After the tissue section was washed 3 times with PBS(−), a solution of 3,3'-diaminobenzidine (DAB, SK-4105, VEC), which is a substrate of the peroxidase, was added, and the section was incubated at room temperature for about 2 minutes to immunologically stain the tissue. The tissue section that developed the color was immersed in distilled water to terminate the reaction, then counterstaining was performed with a hematoxylin solution, and the tissue was enclosed in a non-aqueous mounting medium (MGK-S, Matsunami Glass), and observed under a microscope.

Figure 2:
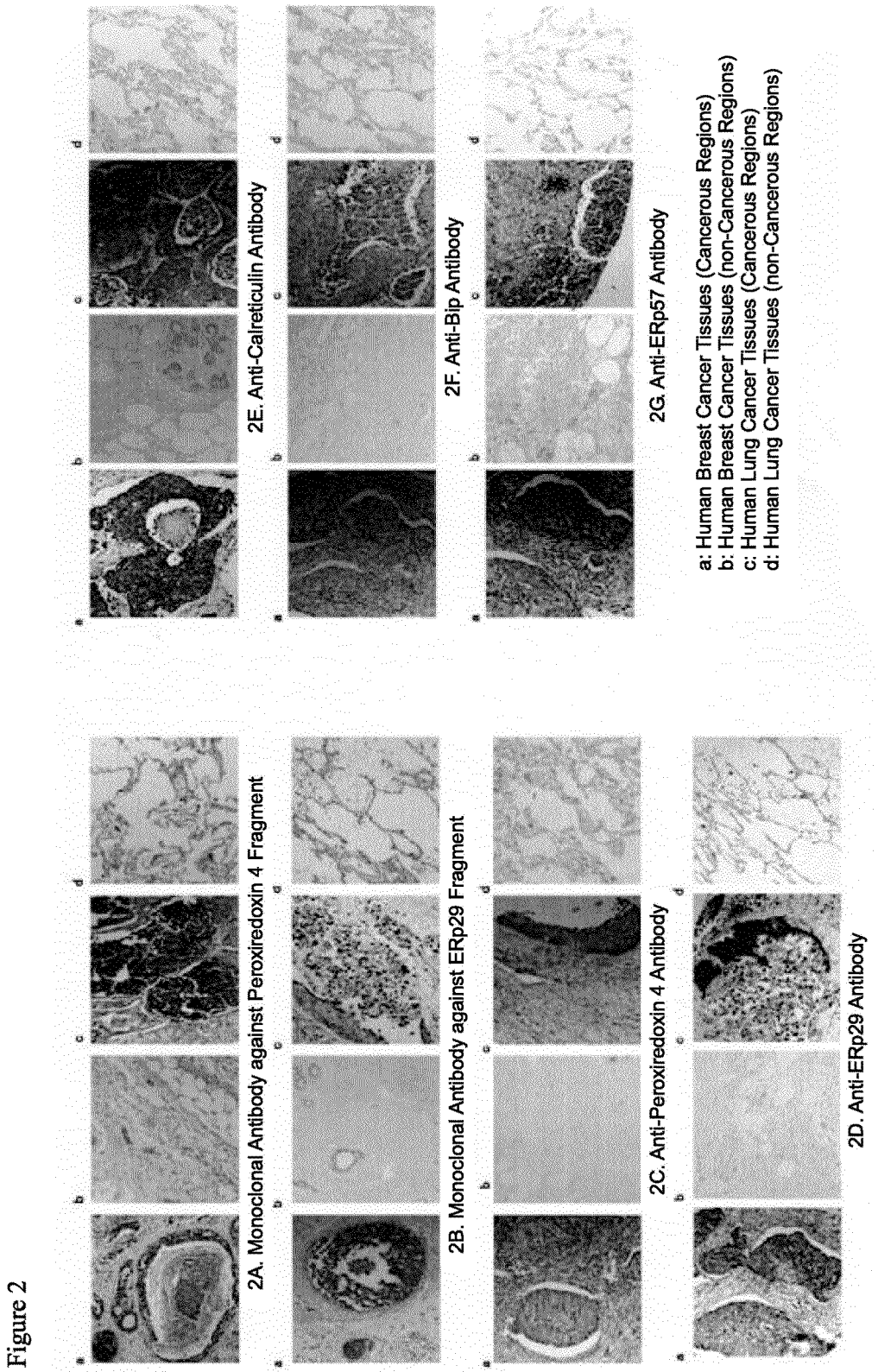
FIG. 2 shows typical histo-immunological staining images obtained by immunologically staining human breast cancer and human lung cancer tissues containing foci of necrosis using various kinds of antibodies against necrotic focus-specific markers in the examples of the present invention. Among the images, the images of a are the staining images of cancerous regions of human breast cancer tissues containing foci of necrosis, and the images of b are the staining images of non-cancerous regions of the same. Among the images, the images of c are the staining images of cancerous regions of human lung cancer tissues containing foci of necrosis, and the images of d are the staining images of non-cancerous regions of the same. The cancer cells including foci of necrosis of human breast cancer and lung cancer tissues were strongly stained with each of the antibodies, and nuclei counterstained with a hematoxylin solution were observed in some places.

The results of the histo-immunological staining are shown in FIG. 2. As a result of immunological staining of cancerous regions and non-cancerous regions of human breast cancer tissues (N=5), and cancerous regions and non-cancerous regions of human lung cancer tissues (N=5) using the monoclonal antibody that recognized the N-terminal peptide of the peroxiredoxin 4 fragment or the N-terminal peptide of ERp29 fragment, strong staining was observed in the foci of necrosis in human breast cancer tissues and human lung cancer tissues and circumferential tissues thereof (FIG. 2A, a and c, and FIG. 2B, a and c), whereas staining was not observed or was weak, even if observed, in the tissues of the non-cancerous regions of human breast cancer and lung cancer (FIG. 2A, b and d, and FIG. 2B, b and d). Further, as a result of the histo-immunological staining of the human tissues performed in a similar manner by using the five kinds of commercial antibodies (primary antibodies) mentioned in Example 2, similar results were obtained with those antibodies, that is, strong staining was observed in the foci of necrosis of the human breast cancer tissues and human lung cancer tissues, and circumferential tissues thereof, whereas staining was not observed or was weak, even if observed, in the human tissues of the non-cancerous regions (FIGS. 2C to 2G).

As a typical clone of the clones of the aforementioned anti-ERp29-specific monoclonal antibody-producing hybridomas, the hybridoma that produces a mouse monoclonal antibody against the human ERp29 fragment as a necrosis marker (code: YKERp C6707 FCS(+)) was deposited at the Incorporated Administrative Agency, National Institute of Evaluation, Patent Microorganisms Depositary, 2-5-8 Kazusakamatri, Kisarazu-shi, Chiba, 292-0818, Japan under the provisions of the Budapest Treaty on the International Recognition of the Deposit of Microorganisms for the Purposes of Patent Procedure. The deposition was confirmed by this depositary with an accession number of NITE ABP-1063 (receiving date: Jan. 20, 2011).

Example 5

Purification of Monoclonal Antibody

The anti-human ERp29 monoclonal antibody was purified from the culture supernatant of the hybridoma YKERp C6707 FCS(+) with a protein A column. Specifically, 50 ml of the culture supernatant was added to 1 ml of HiTrapA column equilibrated with PBS(−), and after the column was washed with 5 ml of PBS(−), eluted from the column with a 0.17 M buffer (pH 2.3). One-milliliter eluted fractions were collected with monitoring absorbance at 280 nm, and proteins in the fractions showing a high absorbance were quantified by the Bradford method (Bio-Rad), and a purified monoclonal antibody was obtained.

Example 6

Determination of Isotype of Monoclonal Antibody

Isotype of the anti-human ERp29 monoclonal antibody purified in Example 5 was confirmed by using a mouse monoclonal antibody isotyping kit (MMT1, Serotec). The purified monoclonal antibody (150 μl) was added to a reaction tube, and reacted at room temperature for 30 seconds according to the attached manual. The reaction mixture was sufficiently mixed on a vortex mixer, and then an isotyping strip was put into the reaction tube to determine the isotype. As a result, the isotype of the anti-human ERp29 monoclonal antibody was determined to be IgG2a/κ.

Example 7

Detection of Cancerous Region in Cancer-Bearing Mouse Using Radiation-Labeled Monoclonal Antibody 1) Labeling of Anti-Human ERp29 Monoclonal Antibody with In-111

Figure 3:
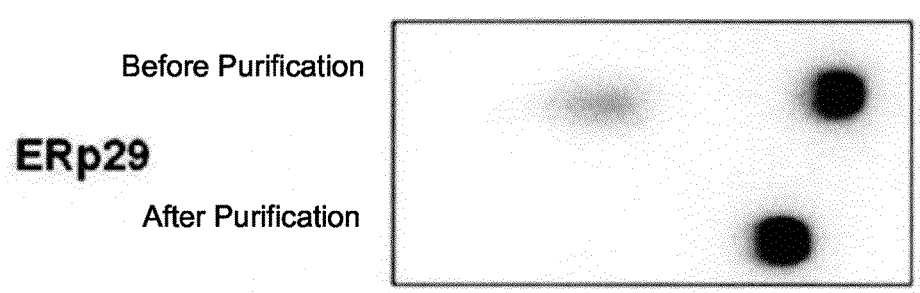
FIG. 3 shows an autoradiographic image of DTPA-IgG before and after purification electrophoresed by cellulose acetate electrophoresis.

Each IgG antibody dissolved in a 0.05 M borate buffer (pH 8.5) and N—[(R)-2-amino-3-p-isothiocyanato-phenyl]propyl]-trans-(S,S)-cyclohexane-1,2-diamine-pentaacetic acid (DTPA) dissolved in 0.05 M borate buffer (pH 8.5) were mixed at a ratio of 1:2.5 on a molecular weight basis, and the reaction was allowed at 37° C. for 16 hours. Indium chloride ([In-111]$Cl_3$) was mixed with an equal amount of 1 M acetate buffer (pH 6.0), the mixture was left standing at room temperature for 5 minutes and mixed with an equal amount of the aforementioned reaction mixture of DTPA and IgG, and the mixture was left standing at room temperature for 30 minutes. [In-111]DTPA-IgG and [In-111]DTPA were separated by cellulose acetate electrophoresis, and the number of DTPA binding to IgG was calculated. The aforementioned reaction mixture of DTPA and IgG was applied to a Sephadex G50 carrier to remove unbound DTPA and thereby purify DTPA-IgG. This purified DTPA-IgG was labeled with In-111 by the method described above, and unreacted In-111 was removed by using a Sephadex G50 carrier to obtain [In-111]DTPA-IgG By using this [In-111]DTPA-IgG, the following experiments were performed. FIG. 3 shows an autoradiographic image of DTPA-IgG before and after purification electrophoresed by cellulose acetate electrophoresis.

Figure 4:
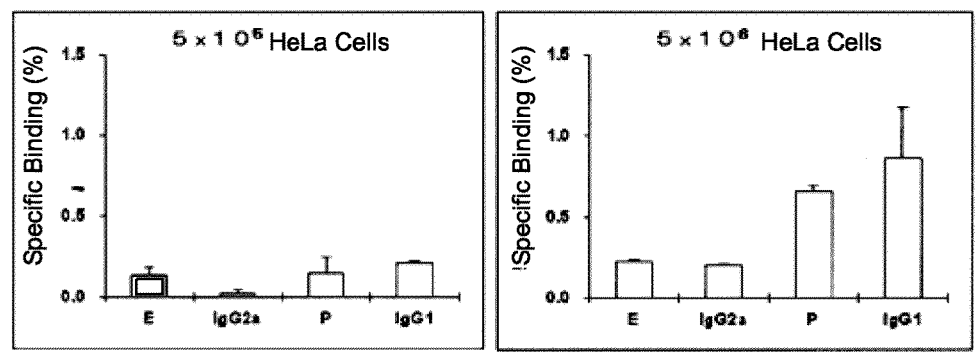
FIG. 4 shows the results of measurement of reactions of In-111-labeled monoclonal antibodies and live HeLa cells by using a gamma counter.

2) Reaction of In-111-Labeled Monoclonal Antibody with Live Hela Cells $5×10^5$ or $5×10^6$ of the HeLa cells were suspended in 1% BSA/PBA, [In-111]DTPA-IgG was added to the suspension, the mixture was incubated on ice for 1 hour, the cells were washed with PBS, and radioactivity bound to the HeLa cells was measured with a gamma counter. As a result, it was found that the labeled anti-human ERp29 monoclonal antibody did not bind to the live HeLa cells. FIG. 4 shows specific binding ratios of the In-111-labeled monoclonal antibody (represented by P) bound by contacting it with $5×10^5$ of the HeLa cells (left graph) or $5×10^6$ of the HeLa cells (right graph). IgG2a, E, and IgG1 represent negative controls using other antibodies. Since ERp29 is an intracellular protein, it is reasonable that it did not bind with the HeLa cells, and it served as one basis for performing the examination using cancer-bearing animals described below.

3) Imaging in Cancer-Bearing Mouse Using In-111-Labeled Monoclonal Antibody

Figure 5:
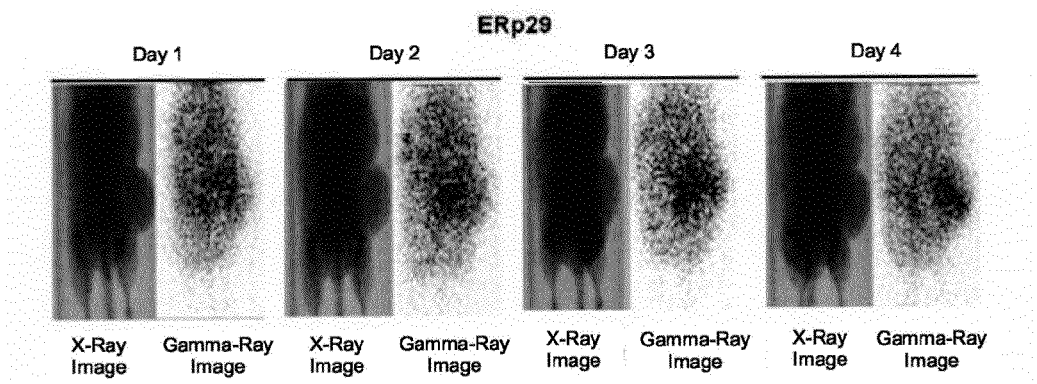
FIG. 5 shows X-ray photographs showing the results of imaging in cancer-bearing mice using the In-111-labeled monoclonal antibody.

The HeLa cells were subcutaneously transplanted into a BALB/c-nu/nu mouse to form a tumor. [In-111]DTPA-IgG (50 μCi, protein amount was adjusted to 12 μg with unlabeled IgG) was administered from the caudal vein, and X-ray images and gamma-ray images were obtained on the days 1, 2, 3, and 4 after the administration. It was revealed that [In-111]DTPA-IgG accumulated in a part of the tumor with time. FIG. 5 shows the X-ray images (left) and the gamma-ray images (right) of the cancer-bearing mouse obtained by anesthetizing the mouse by inhalation and fixing it with a tape. In FIG. 5, the X-ray images (left) and the gamma-ray images (right) on the days 1, 2, 3, and 4 are shown from the left. In the X-ray images (left) of the cancer-bearing mouse on the days 1 to 4 shown in FIG. 5, the sufficiently grown human cancer is imaged in the shape of bossing near the right buttock. Further, in the gamma-ray images (right), distinct accumulation of the labeled anti-ERp29 is observed in the tumor of the nude mouse, which is especially distinct in the images on the day 2 to 4.

4) Confirmation of Accumulation Site of In-111-Labeled Monoclonal Antibody

Figure 6:
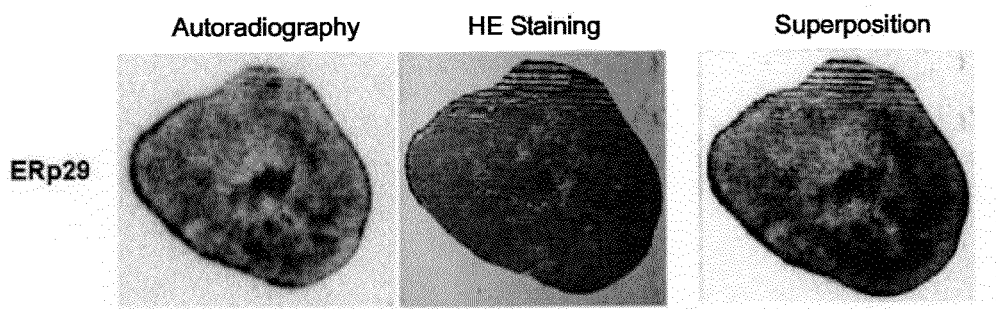
FIG. 6 shows the results of autoradiography and hematoxylin-eosin staining (HE staining) conducted for adjacent samples among a plurality of frozen samples of tumor, which were prepared for the tumor extracted after the imaging on the day 4 after the administration of the In-111-labeled monoclonal antibody.

After imaging on the day 4 after the administration of [In-111]DTPA-IgG, the tumor was extracted to prepare a plurality of frozen samples, and autoradiography and hematoxylin-eosin staining (HE staining) were performed for adjacent samples among the plurality of the prepared samples. In FIG. 6, the autoradiographic image, the HE staining image, and an image obtained by superposing the foregoing two images are shown from the left. In the HE staining of the tumor section, the necrotic part around the center was stained scarcely in blue, but stained weakly in red, and the outer normal carcinoma tissue part and the circumferential part of the necrotic focus surrounding the center were stained in reddish blue. As shown in FIG. 6, it was revealed that [In-111]DTPA-IgG selectively accumulated in the circumferential part of the necrotic focus surrounding the necrotic part at the center of the extracted tumor (size: about 13.6 mm×18.3 mm). That is, from the image obtained by superposing the autoradiographic image and the HE staining image, it was judged that accumulation of the In-111-labeled monoclonal antibody was observed in the circumferential part of the necrotic focus surrounding the focus of necrosis around the center.

Figure 7:
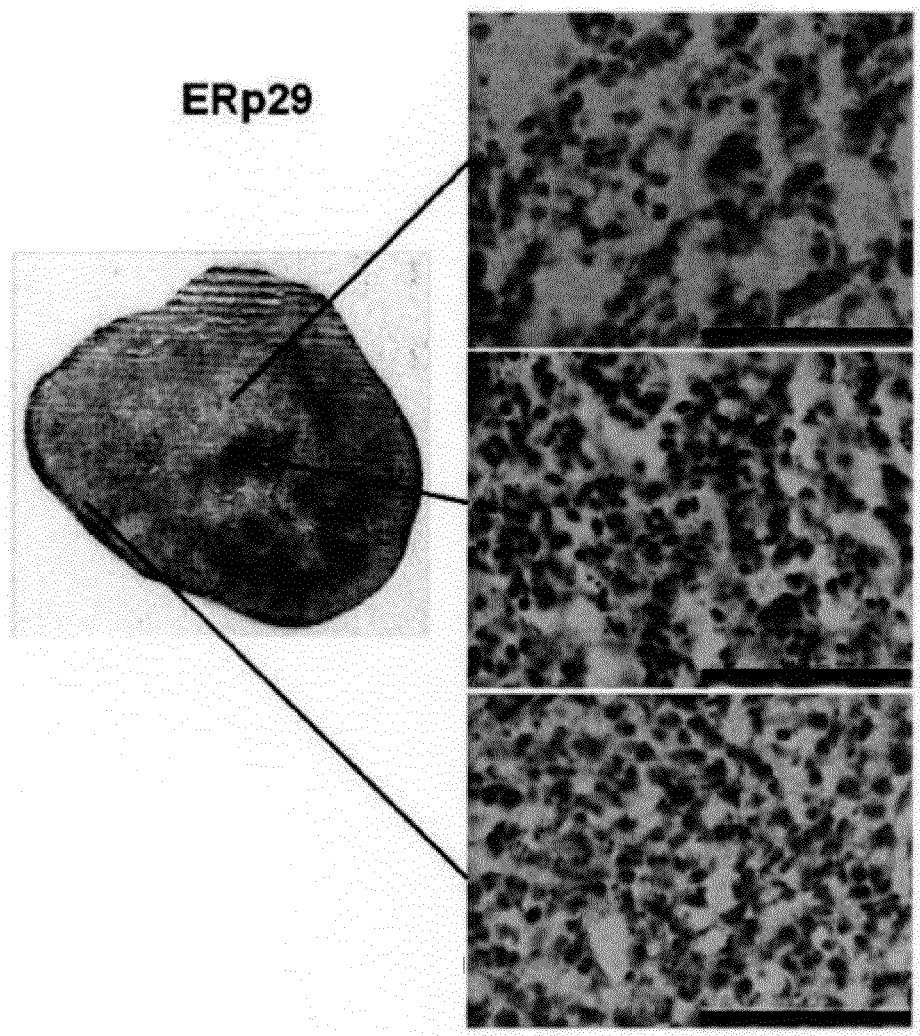
FIG. 7 shows morphology of cell in a circumferential region of a focus of necrosis in which the In-111-labeled monoclonal antibodies accumulated.

5) Cell Morphology in in-111-Labeled Monoclonal Antibody-Accumulating Circumferential Part of Focus of Necrosis From the pathology of the extracted tumor, it was revealed that [In-111]DTPA-IgG accumulated in the necrotic cells in which the nuclei remained, and did not accumulate in cells of which nuclei were deficient. It seems that this indicated that the necrosis marker protein remained in the cells of which necrosis occurred not so much ago, and the neighborhood thereof. That is, in FIG. 7, it can be seen that, in the necrotic part around the center, cell morphology collapsed and nuclei were not observed; in the circumferential part of the necrotic part, although nuclei of the cells could be observed, but morphology of them was different from that of normal cancer cells; and in the circumferential part around the outside of the tumor, nuclei and cytoplasm were clearly observed, and the cells were in the morphology of normal cancer cells. The bars in the images indicate 100 μm.

INDUSTRIAL APPLICABILITY

By using an antibody of the present invention against a necrosis marker, for example, a protein or a fragment thereof, there can be provided a novel measurement kit with which a focus of necrosis that is recognized by the antibody or a state of progress of a pathological condition as the cause of the necrosis can be conveniently and quickly measured. As such a focus of necrosis, not only foci of necrosis (tissues) of various solid carcinomas, myocardial infarction, and cerebral infarction, but foci of necrosis in postnecrotic cirrhosis, necrotizing pancreatitis, necrotising fasciitis, and so forth, and further, foci of necrosis in arteriosclerotic gangrene, diabetic gangrene and obstructive gangrene can also be an object of the kit.

As a result, development of a detection kit that can be used for a wider range of diseases compared with various carcinoma markers etc. in view of necrosis of lesions, or a therapeutic agent targeting necrosis part in such diseases is enabled. For example, if an artificial antibody such as a lower molecular weight antibody is prepared, such an antibody can be more easily incorporated into cells because it has a smaller molecular weight, whereas it is difficult to incorporate a conventional molecular weight antibody into cells because it has a large molecular weight. Further, such a low molecular weight antibody is considered to show higher tissue migration properties, and therefore useful as an active component/ingredient of a kit for diagnostic imaging or a pharmaceutical composition.

The invention claimed is:

1. A monoclonal antibody, which is produced by a hybridoma having accession number NITE ABP-1063.

2. A kit used for detecting a focus of necrosis, which comprises the monoclonal antibody according to claim 1.

3. A conjugate for diagnostic imaging or a therapeutic treatment, which consists of the monoclonal antibody according to claim 1, and a labeling compound or a therapeutically effective compound.

4. A kit for use in diagnostic imaging or a pharmaceutical composition, which comprises the conjugate according to claim 3 as an active component/ingredient.

* * * * *

SEQUENCE LISTING

```
<160> NUMBER OF SEQ ID NOS: 10

<210> SEQ ID NO 1
<211> LENGTH: 261
<212> TYPE: PRT
<213> ORGANISM: Homo sapiens

<400> SEQUENCE: 1
```

Met Ala Ala Ala Val Pro Arg Ala Ala Phe Leu Ser Pro Leu Leu Pro
1               5                   10                  15

Leu Leu Leu Gly Phe Leu Leu Ser Ala Pro His Gly Gly Ser Gly
            20                  25                  30

Leu His Thr Lys Gly Ala Leu Pro Leu Asp Thr Val Thr Phe Tyr Lys
            35                  40                  45

Val Ile Pro Lys Ser Lys Phe Val Leu Val Lys Phe Asp Thr Gln Tyr
50                  55                  60

Pro Tyr Gly Glu Lys Gln Asp Glu Phe Lys Arg Leu Ala Glu Asn Ser
65                  70                  75                  80

Ala Ser Ser Asp Asp Leu Leu Val Ala Glu Val Gly Ile Ser Asp Tyr
                85                  90                  95

Gly Asp Lys Leu Asn Met Glu Leu Ser Glu Lys Tyr Lys Leu Asp Lys
                100                 105                 110

Glu Ser Tyr Pro Val Phe Tyr Leu Phe Arg Asp Gly Asp Phe Glu Asn
            115                 120                 125

Pro Val Pro Tyr Thr Gly Ala Val Lys Val Gly Ala Ile Gln Arg Trp
            130                 135                 140

Leu Lys Gly Gln Gly Val Tyr Leu Gly Met Pro Gly Cys Leu Pro Val
145                 150                 155                 160

Tyr Asp Ala Leu Ala Gly Glu Phe Ile Arg Ala Ser Gly Val Glu Ala
                165                 170                 175

Arg Gln Ala Leu Leu Lys Gln Gly Gln Asp Asn Leu Ser Ser Val Lys
                180                 185                 190

Glu Thr Gln Lys Lys Trp Ala Glu Gln Tyr Leu Lys Ile Met Gly Lys
            195                 200                 205

Ile Leu Asp Gln Gly Glu Asp Phe Pro Ala Ser Glu Met Thr Arg Ile
            210                 215                 220

Ala Arg Leu Ile Glu Lys Asn Lys Met Ser Asp Gly Lys Lys Glu Glu
225                 230                 235                 240

Leu Gln Lys Ser Leu Asn Ile Leu Thr Ala Phe Gln Lys Lys Gly Ala
                245                 250                 255

Glu Lys Glu Glu Leu
            260

<210> SEQ ID NO 2
<211> LENGTH: 240
<212> TYPE: PRT
<213> ORGANISM: Homo sapiens

<400> SEQUENCE: 2

Met Val His Thr Lys Gly Ala Leu Pro Leu Asp Thr Val Thr Phe Tyr
1               5                   10                  15

Lys Val Ile Pro Lys Ser Lys Phe Val Leu Val Lys Phe Asp Thr Gln
                20                  25                  30

Tyr Pro Tyr Gly Glu Lys Gln Asp Glu Phe Lys Arg Leu Ala Glu Asn
            35                  40                  45

Ser Ala Ser Ser Asp Asp Leu Leu Val Ala Glu Val Gly Ile Ser Asp
50                  55                  60

Tyr Gly Asp Lys Leu Asn Met Glu Leu Ser Glu Lys Tyr Lys Leu Asp
65                  70                  75                  80

Lys Glu Ser Tyr Pro Val Phe Tyr Leu Phe Arg Asp Gly Asp Phe Glu
                85                  90                  95

Asn Pro Val Pro Tyr Thr Gly Ala Val Lys Val Gly Ala Ile Gln Arg

```
              100                 105                 110
Trp Leu Lys Gly Gln Gly Val Tyr Leu Gly Met Pro Gly Cys Leu Pro
            115                 120                 125

Val Tyr Asp Ala Leu Ala Gly Glu Phe Ile Arg Ala Ser Gly Val Glu
130                 135                 140

Ala Arg Gln Ala Leu Leu Lys Gln Gly Gln Asp Asn Leu Ser Ser Val
145                 150                 155                 160

Lys Glu Thr Gln Lys Lys Trp Ala Glu Gln Tyr Leu Lys Ile Met Gly
            165                 170                 175

Lys Ile Leu Asp Gln Gly Glu Asp Phe Pro Ala Ser Glu Met Thr Arg
            180                 185                 190

Ile Ala Arg Leu Ile Glu Lys Asn Lys Met Ser Asp Gly Lys Lys Glu
            195                 200                 205

Glu Leu Gln Lys Ser Leu Asn Ile Leu Thr Ala Phe Lys Lys Gly
            210                 215                 220

Ala Glu Lys Glu Glu Leu Gly Ser Arg Ser His His His His His His
225                 230                 235                 240

<210> SEQ ID NO 3
<211> LENGTH: 264
<212> TYPE: PRT
<213> ORGANISM: Homo sapiens

<400> SEQUENCE: 3

Met Ala Ala Ala Cys Thr Pro Arg Ala Pro Phe Pro Trp Ile Arg
1                   5                   10                  15

Ser Leu Ser Thr Arg Gly Pro Leu Gly Arg Gly Ile Ser Pro Lys Ser
                20                  25                  30

Pro Trp Asn Thr His Leu Leu Ser Ser Ile Arg Pro Gln Val Ile Pro
            35                  40                  45

Lys Ser Lys Phe Val Leu Val Lys Phe Asp Thr Gln Tyr Pro Tyr Gly
50                  55                  60

Glu Lys Gln Asp Glu Phe Lys Arg Leu Ala Glu Asn Ser Ala Ser Ser
65                  70                  75                  80

Asp Asp Leu Leu Val Ala Glu Val Gly Ile Ser Asp Tyr Gly Asp Lys
                85                  90                  95

Leu Asn Met Glu Leu Ser Glu Lys Tyr Lys Leu Asp Lys Glu Ser Tyr
            100                 105                 110

Pro Val Phe Tyr Leu Phe Arg Asp Gly Asp Phe Glu Asn Pro Val Pro
            115                 120                 125

Tyr Thr Gly Ala Val Lys Val Gly Ala Ile Gln Arg Trp Leu Lys Gly
130                 135                 140

Gln Gly Val Tyr Leu Gly Met Pro Gly Cys Leu Pro Val Tyr Asp Ala
145                 150                 155                 160

Leu Ala Gly Glu Phe Ile Arg Ala Ser Gly Val Glu Ala Arg Gln Ala
                165                 170                 175

Leu Leu Lys Gln Gly Gln Asp Asn Leu Ser Ser Val Lys Glu Thr Gln
            180                 185                 190

Lys Lys Trp Ala Glu Gln Tyr Leu Lys Ile Met Gly Lys Ile Leu Asp
            195                 200                 205

Gln Gly Glu Asp Phe Pro Ala Ser Glu Met Thr Arg Ile Ala Arg Leu
210                 215                 220

Ile Glu Lys Asn Lys Lys Arg Ser Cys Lys Lys Ala Val Cys Asp Phe
225                 230                 235                 240
```

-continued

```
Pro Gly Phe Gly Gly Gly Arg Glu Gly Arg Val Asn Leu Leu Ala Val
            245                 250                 255

Ser Pro Leu Trp Asn Ile Arg Gly
        260

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Trp Glu Thr Glu Glu Arg Pro Arg Thr
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Leu His Thr Lys Gly Ala Leu Pro Leu
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide

<400> SEQUENCE: 6

Trp Glu Thr Glu Glu Arg Pro Arg Thr Cys
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide

<400> SEQUENCE: 7

Leu His Thr Lys Gly Ala Leu Pro Leu Cys
1               5                   10

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide

<400> SEQUENCE: 8

Trp Glu Thr Glu Glu Arg Pro Arg
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide
```

```
<400> SEQUENCE: 9

Leu His Thr Lys Gly Ala Leu Pro
1               5

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide

<400> SEQUENCE: 10

Gly Ala Val Gln Gly Trp Glu Thr Glu Arg Pro Arg Thr Cys
1               5                   10                  15
```